United States Patent
Galliano et al.

(10) Patent No.: US 10,145,229 B2
(45) Date of Patent: *Dec. 4, 2018

(54) SURFACE SOLIDS SYSTEM

(71) Applicant: HALLIBURTON ENERGY SERVICES, INC., Houston, TX (US)

(72) Inventors: Clinton Cheramie Galliano, Houma, LA (US); Mathew Dennis Rowe, Lafayette, LA (US); Walter Varney Andrew Graves, Lafayette, LA (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/129,487

(22) PCT Filed: Dec. 29, 2014

(86) PCT No.: PCT/US2014/072477
§ 371 (c)(1),
(2) Date: Sep. 27, 2016

(87) PCT Pub. No.: WO2016/108808
PCT Pub. Date: Jul. 7, 2016

(65) Prior Publication Data
US 2017/0175511 A1   Jun. 22, 2017

(51) Int. Cl.
*E21B 47/00* (2012.01)
*E21B 47/12* (2012.01)
(Continued)

(52) U.S. Cl.
CPC .............. *E21B 47/00* (2013.01); *B01D 33/03* (2013.01); *B01D 33/80* (2013.01); *B04B 13/00* (2013.01);
(Continued)

(58) Field of Classification Search
CPC ........ B01D 33/03; B01D 33/80; B04B 13/00; B04C 11/00; E21B 47/00; E21B 21/065
See application file for complete search history.

(56) References Cited

U.S. PATENT DOCUMENTS

| 4,413,511 A | 11/1983 | Godbey et al. |
| 6,357,536 B1 | 3/2002 | Schrader et al. |

(Continued)

OTHER PUBLICATIONS

Dupriest et al., Exclusive roundup of abstracts from 18 technical sessions, retrieved from the internet at: http://www.drillingcontractor.org/exclusive-roundup-of-abstracts-from-18-technical-sessions-2-3979, at least as early as Jan. 2010, 25 pages.

(Continued)

*Primary Examiner* — Alexander Satanovsky
*Assistant Examiner* — Lina M Cordero
(74) *Attorney, Agent, or Firm* — Kilpatrick Townsend & Stockton LLP (57) ABSTRACT

Systems and methods are provided for monitoring micro-electro-mechanical ("MEM") devices removed from a fluid flow stream from a wellbore by a component of solids control equipment used with a drilling operation. The system can include a first MEM reader. The system can also include a second MEM reader. The first MEM reader can be positionable proximate to the fluid flow stream for detecting MEM devices in the fluid flow stream. The second MEM reader can be positionable proximate to the fluid flow stream and between the fluid flow output and the wellbore for detecting at least a subset of the MEM devices in the fluid flow stream. The system can further include a computing device for determining an amount and types of the MEM devices removed from the fluid flow stream by the component of solids control equipment.

15 Claims, 7 Drawing Sheets

(51) Int. Cl.
- *B01D 33/03* (2006.01)
- *B01D 33/80* (2006.01)
- *B04B 13/00* (2006.01)
- *B04C 11/00* (2006.01)
- *E21B 21/06* (2006.01)

(52) U.S. Cl.
CPC ............ *B04C 11/00* (2013.01); *E21B 21/065* (2013.01); *E21B 47/122* (2013.01)

(56) References Cited

U.S. PATENT DOCUMENTS

| | | | |
|---|---|---|---|
| 6,607,659 B2 * | 8/2003 | Hensley | E21B 21/065 175/206 |
| 6,745,833 B2 | 6/2004 | Aronstam et al. | |
| 6,823,238 B1 * | 11/2004 | Hensley | E21B 21/06 210/113 |
| 6,993,432 B2 | 1/2006 | Jenkins et al. | |
| 8,162,050 B2 * | 4/2012 | Roddy | E21B 33/13 166/250.14 |
| 8,172,007 B2 | 5/2012 | Dolman et al. | |
| 8,292,187 B2 | 10/2012 | Getliff | |
| 8,297,352 B2 | 10/2012 | Roddy et al. | |
| 8,397,810 B2 | 3/2013 | Kilchrist et al. | |
| 9,023,275 B2 * | 5/2015 | McClung, III | E21B 21/065 422/22 |
| 9,488,019 B1 * | 11/2016 | Rowe | C09K 8/03 |
| 9,759,645 B2 * | 9/2017 | Rowe | E21B 47/00 |
| 2007/0285275 A1 | 12/2007 | Purkis et al. | |
| 2008/0316049 A1 * | 12/2008 | Verret | E21B 47/1015 340/854.6 |
| 2009/0087912 A1 | 4/2009 | Ramos et al. | |
| 2009/0151939 A1 * | 6/2009 | Bailey | E21B 47/12 166/255.1 |
| 2009/0301778 A1 | 12/2009 | Taylor | |
| 2010/0044034 A1 | 2/2010 | Bailey et al. | |
| 2010/0139386 A1 | 6/2010 | Taylor | |
| 2010/0258304 A1 * | 10/2010 | Hegeman | E21B 47/10 166/250.01 |
| 2010/0268470 A1 | 10/2010 | Kamal et al. | |
| 2010/0274546 A1 | 10/2010 | Zafari et al. | |
| 2011/0186290 A1 * | 8/2011 | Roddy | E21B 43/25 166/253.1 |
| 2011/0187556 A1 * | 8/2011 | Roddy | G01V 3/00 340/853.3 |
| 2011/0192592 A1 * | 8/2011 | Roddy | E21B 47/01 166/250.01 |
| 2011/0192594 A1 * | 8/2011 | Roddy | E21B 33/13 166/250.01 |
| 2011/0192598 A1 * | 8/2011 | Roddy | E21B 33/13 166/253.1 |
| 2011/0199228 A1 * | 8/2011 | Roddy | E21B 33/13 340/856.4 |
| 2011/0277996 A1 | 11/2011 | Cullick et al. | |
| 2012/0132418 A1 | 5/2012 | McClung et al. | |
| 2012/0178653 A1 | 7/2012 | McClung et al. | |
| 2013/0054146 A1 | 2/2013 | Rasmus et al. | |
| 2013/0062261 A1 * | 3/2013 | Bailey | B07B 1/28 209/240 |
| 2013/0213903 A1 * | 8/2013 | Bailey | B07B 1/28 210/780 |
| 2013/0256032 A1 | 10/2013 | Palmer et al. | |
| 2013/0261971 A1 | 10/2013 | Ramirez et al. | |

OTHER PUBLICATIONS

Gaukler et al., RFID Solutions for the Upstream oil & Gas Supply Chain, Jan. 2009, 13 pages.

Lamarre et al., Using Passive Integrated Transponder (PIT) Tags to Investigate Sediment Transport in Grave-Bed Rivers, Abstract, Jul. 2005, 1 page.

International Patent Application No. PCT/US2014/072477, International Search Report and Written Opinion, dated Aug. 27, 2015, 7 pages.

Slaton, Drilling Rig Advances, retrieved from the internet at "http://www.cybermanual.com/in-large-and-small-steps-new-technology-and-newbuilds-re.html?p.=9" at least as early as Sep. 21, 2016, 18 pages.

* cited by examiner

SURFACE SOLIDS SYSTEM

CROSS-REFERENCE TO RELATED APPLICATIONS

This is a U.S. national phase under 35 U.S.C. 371 of International Patent Application No. PCT/US2014/072477, titled "Surface Solids System" and filed Dec. 29, 2014, the entirety of which is incorporated herein by reference.

TECHNICAL FIELD

The present disclosure relates generally to determining or monitoring efficiency of solids control equipment for use in well systems. More specifically, but not by way of limitation, this disclosure relates to monitoring micro-electro-mechanical ("MEM") devices removed from a fluid flow stream from a wellbore by a component of solids control equipment used with a drilling operation.

BACKGROUND

A well system (e.g., oil or gas wells for extracting fluids from a subterranean formation) can include a drilling rig for drilling in a wellbore, along with other components or equipment. Fluid from the drilling operation, such as drilling fluid or drilling mud, can flow to solids control equipment that can be used to remove non-desirable solids from the fluid prior to reintroducing the fluid into the wellbore for the drilling operation. Efficiently removing non-desirable solids from the fluid flow stream can enhance the drilling operations on a wellbore and can help maintain high-quality drilling fluid properties.

DETAILED DESCRIPTION

Certain aspects and features of the present disclosure are directed to monitoring micro-electro-mechanical ("MEM") devices removed from a fluid flow stream from a wellbore by a component of solids control equipment. During drill rig operations, the drilling fluid circulation system or mud system circulates drilling fluid or mud through the wellbore. Circulating the drilling fluid may lift non-desirable solids, such as cuttings and other debris in the wellbore, to a surface of the wellbore as the drilling fluid circulates to the surface. Once the drilling fluid reaches the surface, the fluid is processed to maintain the drilling fluid's properties, such as the fluid's density, before the fluid is pumped back into the wellbore. Solids control equipment, such as shale shakers, desilters, desanders, centrifuges, mud cleaners, or any combination thereof, may be used to process the drilling fluid by removing the non-desirable solids from the fluid flow stream from the wellbore. The efficiency of the solids control equipment may be monitored using MEM readers and MEM devices of different sizes, shapes, and densities that can represent certain types of non-desirable solids in the drilling fluid. The efficiency of solids control equipment in removing MEM devices of a size, shape, or density may be representative of the efficiency of removing non-desirable solids of the same amount and type as the MEM devices.

For example, a known quantity and known types of MEM devices (e.g., devices with radio frequency identification ("RFID") tags) of different sizes, shapes, and densities may be placed in a fluid flow stream between a wellbore and a solids control equipment. In other examples, an unknown quantity and unknown types of MEM devices can be used. A MEM reader (e.g., an RFID tag reader) can detect an amount and types of MEM devices in the fluid flow stream prior to the fluid with the MEM devices entering the solids control equipment. The MEM reader can transmit this data to a computing device. Another MEM reader can detect an amount and types of MEM devices in the fluid flow stream subsequent to the fluid with the MEM devices exiting the solids control equipment. The other MEM reader can transmit this data to the computing device. The computing device can compare the data about the amount and types of MEM devices in the fluid flow stream before and after the solids control equipment to determine an amount and types of MEM devices removed from the fluid flow stream by the solids control equipment.

The computing device may also compare data about the amount and types of MEM devices in the fluid flow stream before and after the solids control equipment to determine efficiency of the solids control equipment. In some examples, the sizes, shapes, and densities of the MEM devices may be representative of the sizes, shapes, and densities of non-desirable solids in the wellbore. The efficiency of a solids control equipment in removing an amount and types of MEM devices representative of non-desirable solids may correspond to the efficiency of the solids control equipment in removing non-desirable solids of the same amount and types as the MEM devices.

The computing device may also compare the amount and types of MEM devices removed by the solids control equipment to a threshold of expected efficiency for the solids control equipment. If the computing device determines that the efficiency of the solids control equipment is below the threshold, the computing device may output an alarm.

Determining and monitoring the efficiency of a solids control equipment in removing non-desirable solids from the fluid flow stream can enhance the drilling operations on a wellbore. For example, improved solids control efficiency may translate into less replacement fluid, fewer additives, less waste to be transported and disposed of, and less risk of hole problems related to excessive solids content in the drilling fluid. Also, effectively removing non-desirable solids from the drilling fluid may help maintain desirable drilling fluid properties, such as fluid viscosity or density.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative examples but, like the illustrative examples, should not be used to limit the present disclosure.

Figure 1:
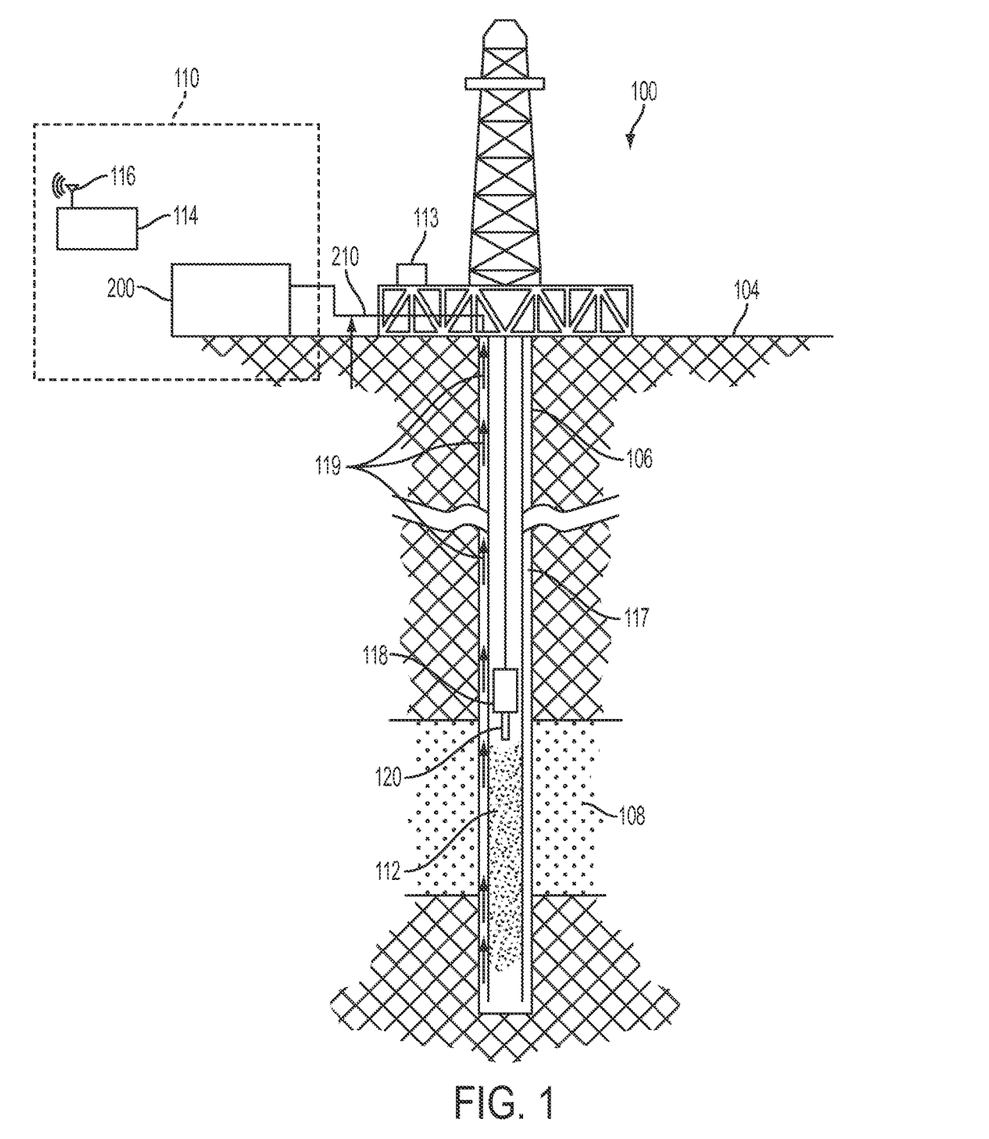
FIG. 1 is a schematic diagram showing a drilling rig on a wellbore along with a system for monitoring removal of micro-electro-mechanical ("MEM") devices representative of non-desirable solids according to one example of the present disclosure.

FIG. 1 is a schematic diagram showing a drilling rig 100 and a wellbore 106 along with a system 110 for monitoring removal of MEM devices representative of non-desirable solids according to one example of the present disclosure.

In this example, drilling rig 100 is depicted for a well system (e.g., an oil or gas well for extracting fluids from a subterranean formation 108). The drilling rig 100 may be used to create a hole or wellbore 106 in the surface 104. The drilling rig includes a pump 113, a drill string 118, and a drill bit 120. The pump 113 can pump a variety of wellbore compositions, such as drilling fluid or drilling mud, through the drill string 118. The drill string 118 can transmit the drilling fluid to the drill bit 120 through which the drilling fluid exits into the wellbore 106.

The wellbore 106 has been drilled from a surface 104 and through subterranean formation 108. As the wellbore 106 is drilled, the drill bit 120 can cut into rocks or sediments in the wellbore 106 and create rock cuttings and non-desirable solids 112. While the drill bit 120 cuts into the wellbore, drilling fluid is pumped through the drill bit 120 and into the wellbore 106 to enhance drilling operations. Pumping drilling fluid into the wellbore 106 may allow the fluid to sweep up non-desirable solids 112 along a flow path 119 as the fluid circulates back to the surface 104 via the wellbore annulus 117.

At the surface 104, the drilling fluid may be processed, to maintain the fluid's desired characteristics, before the pump 113 pumps the fluid back through the drill string 118 and back into the wellbore 106. Processing the drilling fluid may involve use of a component of solids control equipment 200, such as a shale shaker, a desander, a desilter, a centrifuge, a mud cleaner, or any combination thereof, to remove non-desirable solids 112 from a fluid flow stream 210 from the wellbore. The component of solids control equipment 200 may be positionable between the wellbore 106. The system 110, according to some examples, may be used for monitoring removal of MEM devices, representative of the non-desirable solids, from the fluid flow stream 210 from the wellbore.

The system 110, according to certain examples, can include, among other things, a computing device or processing module 114. The computing device 114 can be positioned at the surface 104, below ground, or offsite. The computing device 114 can include a communication device 116 for transmitting and receiving data. The computing device 114 may be used to determine and monitor the efficiency of a solids control equipment.

Figure 2:
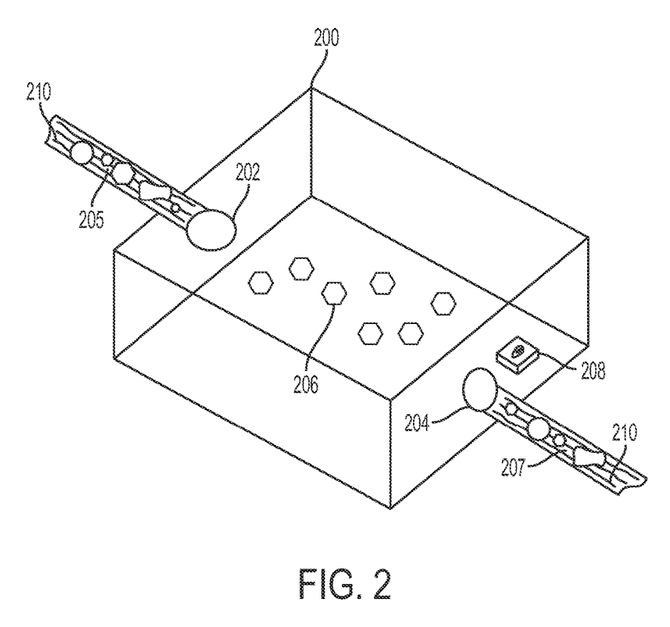
FIG. 2 is a schematic diagram showing a perspective view of a component of solids control equipment, and a MEM reader according to one example of the present disclosure.

FIG. 2 is a perspective view showing a component of solids control equipment 200, MEM devices 205, 206, 207, and a MEM reader 208 according to one example of the present disclosure.

The component of solids control equipment 200 is shown via a transparent view and may be any type of component of solids control equipment. For example, the component of solids control equipment 200 can be a shale shaker, a desander, a desilter, a centrifuge, a mud cleaner or other component of solids control equipment operable in a drill rig system for a wellbore. The component of solids control equipment can have a fluid flow input 202 and a fluid flow output 204. The component of solids control equipment 200 can be positioned near a fluid flow stream 210. The component of solids control equipment 200 may be used to separate non-desirable solids or MEM devices of a size, shape, or density from the fluid flow stream 210 as the fluid flow stream passes from the fluid flow input 202 to the fluid flow output 204. The fluid flow stream 210 can be any fluid flow stream from a wellbore. For example, the fluid flow stream can be a drilling-fluid flow stream used to transport non-desirable solids in the wellbore to a surface of the wellbore.

MEM devices 205, 206, 207 may be any micro-electromechanical devices disposable in a fluid flow stream from a wellbore. For example, the MEM devices can be devices with RFID tags. The MEM devices may also be different sizes, shapes, and densities. In some examples, the sizes, shapes, and densities of the MEM devices may be representative of the sizes, shapes, and densities of non-desirable solids in a wellbore.

The MEM reader 208 can be any reader for detecting MEM devices (e.g., an RFID tag reader). The MEM reader may also detect an amount and type of MEM devices in the fluid flow stream 210. The MEM reader 208 can be positioned near the fluid flow stream 210 and the fluid flow output 204 of the component of solids control equipment 200. In some examples, the MEM reader 208 can be positioned near the fluid flow stream 210 and between the fluid flow output 204 of the component of solids control equipment 200 and a wellbore. The MEM reader 208 may detect MEM devices 207 in the fluid flow stream subsequent to the fluid flow output 204 of the component of solids control equipment 200.

In some examples, a known quantity and known types of MEM devices 205 may be placed in the fluid flow stream 210 prior to the fluid flow input 202. The solids control equipment 200 may separate and capture an amount and types of MEM devices 206 from the fluid flow stream 210 as the fluid flow stream 210 flows from the fluid flow input 202 to the fluid flow output 204. The MEM reader 208 may detect an amount and types of MEM devices 207 in the fluid flow stream 210 subsequent to the fluid flow output 204. In some examples, more than one component of solids control equipment may be used to separate and capture an amount and types of MEM devices from a fluid flow stream. Each component of solids control equipment may be independently associated with a MEM reader. The MEM reader associated with each component of solids control equipment may detect an amount and types of MEM devices in the fluid flow stream subsequent to the fluid flow output of the component of solids control equipment.

In other examples, the MEM devices may be different sizes, shapes, and densities. The MEM reader 208 may detect individual MEM devices and store data that may be representative of a distribution of the amount and types of MEM devices of different sizes, shapes, and densities in the fluid flow stream subsequent to the fluid flow output 204. The distribution may correspond to the amount of each type of MEM device of a different size, shape, or density in the fluid flow stream 210 detected by the MEM reader 208.

Figure 3:
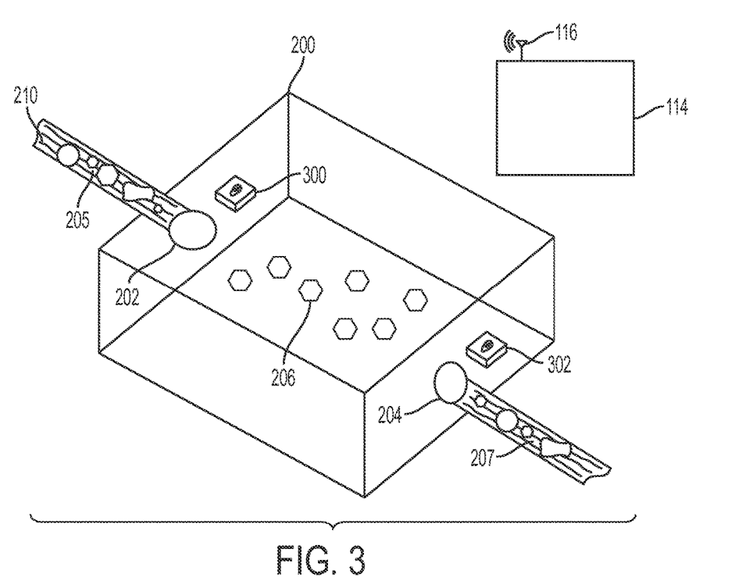
FIG. 3 is a schematic diagram showing a perspective view of a component of solids control equipment and two MEM readers, along with a computing device according to another example of the present disclosure.

Other examples of a system for monitoring efficiency of solids control equipment can use more than one MEM reader. For example, FIG. 3 is a perspective view of a component of solids control equipment 200 and two MEM readers 300, 302, along with a computing device 114 according to one example of the present disclosure.

A first MEM reader 300 may be positioned near a fluid flow stream 210 and between a fluid flow input 202 of the component of solids control equipment 200 and a wellbore. The first MEM reader 300 may detect MEM devices in the fluid flow stream 210 prior to the fluid flow input 202.

A second MEM reader 302 may be positioned near the fluid flow stream 210 and a fluid flow output 204 of the component of solids control equipment 200. In some examples, the second MEM reader 302 may be positioned near the fluid flow stream 201 and between the fluid flow output 204 of the component of solids control equipment 200 and the wellbore. The second MEM reader 302 may detect at least a subset of MEM devices in the fluid flow stream 210 subsequent to the fluid flow output 204.

In some examples, a known quantity and known types of MEM devices 205 may be placed in the fluid flow stream 210 prior to the fluid flow input 202. In other examples, an unknown quantity or unknown types of MEM devices can be used. The first MEM reader 300 may detect an amount and types of MEM devices 205 in the fluid flow stream 210 prior to the fluid flow input 202. The solids control equipment 200 may separate and capture an amount and types of MEM devices 206 from the fluid flow stream 210 as the fluid flow stream 210 flows from the fluid flow input 202 to the fluid flow output 204. The second MEM reader 302 may detect an amount and types of MEM devices 207 in the fluid flow stream 210 subsequent to the fluid flow output 204. In some examples, more than one component of solids control equipment may be used to separate and capture an amount and types of MEM devices from a fluid flow stream. Each component of solids control equipment may be independently associated with a first MEM reader and a second MEM reader. The first MEM associated with each component of solids control equipment may detect an amount and types of MEM devices in the fluid flow stream prior to the fluid flow input of the component of solids control equipment. The second MEM reader associated with each component of solids control equipment may detect an amount and types of MEM devices in the fluid flow stream subsequent to the fluid flow output.

In other examples, the first MEM reader 300 may detect individual MEM devices and store data that may be representative of a distribution of the amount and types of MEM devices of different sizes, shapes, and densities in the fluid flow stream 210 prior to the fluid flow input 202. The second MEM reader 302 may detect individual MEM devices and store data that may be representative of a distribution of the amount and types of MEM devices of different sizes, shapes, and densities in the fluid flow stream 210 subsequent to the fluid flow output 204.

A computing device 114 may transmit to and receive data from the two MEM readers 300, 302. The first MEM reader 300 may transmit data to the computing device 114 through a communication device 116. The data may represent the amount and types of MEM devices 205 in the fluid flow stream 210 prior to the fluid flow input 202. In other examples, the first MEM reader 300 may transmit other data that represents a distribution of the amount and types of MEM devices of different sizes, shapes, and densities in the fluid flow stream 210 prior to the fluid flow input 202.

The second MEM reader 302 may transmit data to the computing device 114 via the communication device 116. The data may represent the amount and types of MEM devices 207 in the fluid flow stream 210 subsequent to the fluid flow output 204. In other examples, the second MEM reader 302 may transmit other data that represents a distribution of the amount and types of MEM devices of different sizes, shapes, and densities in the fluid flow stream 210 subsequent to the fluid flow output 204.

Figure 4:
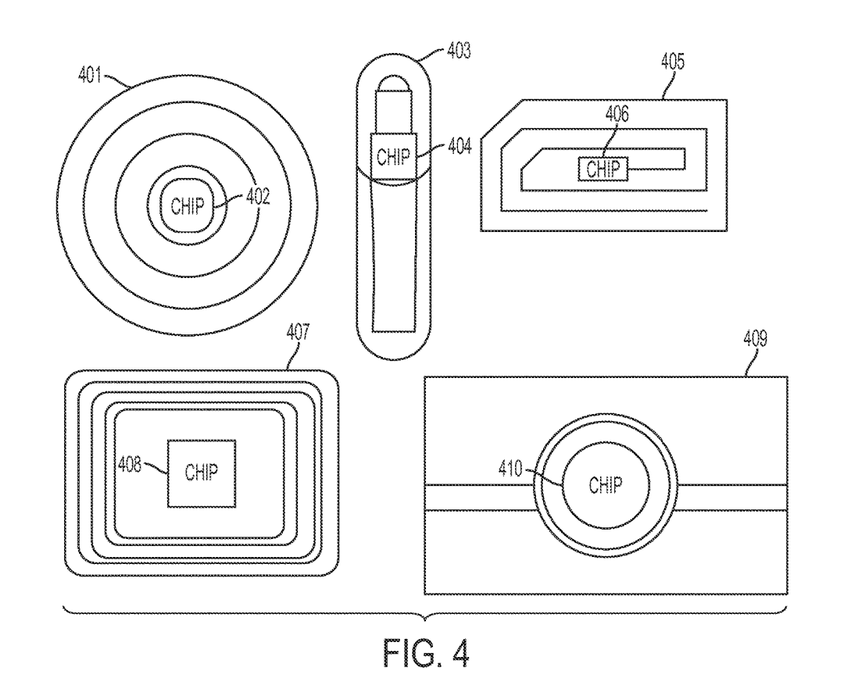
FIG. 4 is a schematic diagram showing a top view of different sized and shaped MEM devices according to one example of the present disclosure.

FIG. 4 is a perspective view of MEM devices 401, 403, 405, 407, 409 of various sizes and shapes according to one example of the present disclosure. The MEM devices may be disposable in a fluid flow stream from a well bore.

In some examples, MEM devices used may be of any shape. The shape of the MEM devices may be representative of any shape of some non-desirable solids in the wellbore. The shape of a MEM device may refer to the external form, appearance or structure of the MEM device. For example, MEM device 401 has a shape that is generally circular or round and may be representative of non-desirable solids in a wellbore having a generally circular or round shape.

MEM devices used in some examples may be of any size. The size of a MEM device may be representative of any size of some non-desirable solids in the wellbore. The size of a MEM device may correspond to the dimensions of a shape of the MEM device. The size of a MEM device may be measured by the area, perimeter, circumference, diameter, length cross section, or the like, of the shape of the MEM device. For example, the sizes of MEM devices 405, 407, 409 may be measured by the area or perimeter of the MEM devices' generally rectangular shapes. The MEM devices 405, 407, 409 may be representative of non-desirable solids in a wellbore having a generally rectangular shape and a similar perimeter, area, or size. In another example, the size of MEM device 403 may be measured by the length of the MEM device's generally cylindrical shape. The MEM device 403 may be representative of non-desirable solids in a wellbore having a generally cylindrical shape and a similar length.

The MEM device may also be of any density. The density of a MEM device may be representative of a density of some non-desirable solids in the wellbore. The density of a MEM device may refer to the volumetric mass density or mass per unit volume of the MEM device. The density of a MEM device may depend on any number of factors including, without limitation, the size of the MEM device, the shape of the MEM device, the components of the MEM device, the material used for manufacturing the MEM device, and other factors. For example, a MEM device can have mechanical (e.g., levers, springs, vibrating structures, etc.), electrical (e.g.., circuits, resistors, capacitors, inductors, etc.) and electro-mechanical components that range in size and affect the density of the MEM device. The MEM devices can also have sensors, actuators, and microelectronics. The MEM devices may also be manufactured from various materials, including, without limitation, silicon, polymers (e.g., poly (methyl methacrylate)), metals (e.g., copper, aluminum, titanium, etc.) ceramics, or other material, which may affect the density of the MEM device. For example, a MEM device manufactured using silicon may have a density of silicon (e.g., approximately 2.3 g/cm$^3$)

The sizes, shapes, or densities of the non-desirable solids that may be represented by the sizes, shapes, or densities of the MEM devices may be determined from solids or visual analysis of the wellbore conducted on-site or off-site.

The MEM devices 401, 403, 405, 407, 409 may also include, or have components integrated onto, a microchip or chip 402, 404, 406, 408, 410, respectively, for storing data. For example, the MEM devices may be devices with RFID tags that use electromagnetic fields to transfer data that may be used to automatically identify and track the RFID tags. The MEM devices can also communicate with and be detected by MEM readers. In some examples, the MEM devices may communicate with and be detected by MEM readers within a proximity from the MEM devices.

Figure 5:
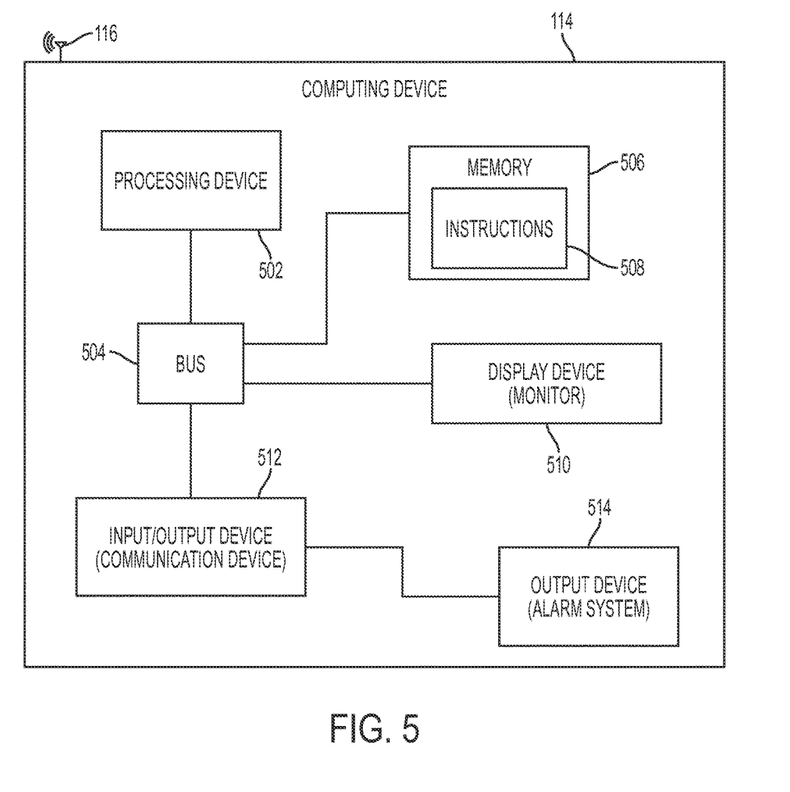
FIG. 5 is a block diagram showing an example of a computing device for determining an amount and types of MEM devices removed from the fluid flow stream by a component of solids control equipment according to one example of the present disclosure.

FIG. 5 is a block diagram of a computing device 114 for determining an amount of MEM devices removed from the fluid flow stream by a component of solids control equipment according to one example of the present disclosure.

The computing device 114 can include a processing device 502 interfaced with other hardware via a bus 504. The computing device 114 may also include a memory device 506. In some examples, the computing device 114 can include input/output interface components (e.g., a display device 510, a communication device 512, and an alarm system 514). The computing device 114 can also include other input/output interface components such as a key board, touch-sensitive surface, mouse and additional storage.

The computing device 114 can receive data from MEM readers via a communication device 116. In some examples, the communication device 116 can represent one or more of any components that facilitate a network connection. In some examples, the communication device may be wireless and can include wireless interfaces such as IEEE 802.11, Bluetooth, or radio interfaces for accessing cellular telephone networks (e.g., transceiver/antenna for accessing a CDMA, GSM, UMTS, or other mobile communications network). In another example, the communication device 116 can be wired and can include interfaces such as Ethernet, USB, IEEE 1394, or a fiber optic interface.

The processing device 502 can include one processing device or multiple processing devices. The processing device 502 can execute one or more efficiency operations for monitoring MEM devices removed from a fluid flow stream from a wellbore by a component of solids control equipment.

The processing device 502 can execute one or more efficiency operations for comparing an amount and types of MEM devices in the fluid flow stream prior to a fluid flow input of a component of solids control equipment and an amount and types of MEM devices in the fluid flow stream subsequent to a fluid flow output of the component of solids control equipment. The efficiency operations can be executed for using the comparison for determining an amount and types of the MEM devices removed from the fluid flow stream by the component of solids control equipment.

In another example, the processing device 502 can execute one more efficiency operations for generating a distribution of the amount and types of MEM devices of different sizes, shapes, and densities in the fluid flow stream prior to the fluid flow input. The processing device 502 can also execute efficiency operations for generating a distribution of the amount and types of MEM devices of different sizes, shapes, and densities in the fluid flow stream subsequent to the fluid flow output. The processing device 502 may also execute an efficiency operation for comparing the two distributions to determine the amount and types of MEM devices of different sizes, shapes, and densities removed from the fluid flow stream by the component of solids control equipment.

In certain examples, the shapes, sizes, and densities of the MEM devices are representative of non-desirable solids in a wellbore to be removed from the fluid flow stream by the component of solids control equipment. The processing device 502 can execute an efficiency operation for determining an amount of MEM devices of a shape, size or density, representative of the non-desirable solids, removed from the fluid flow stream by the component of solids control equipment. The processing device may also execute an efficiency operation for determining the efficiency of the solids control component in removing the non-desirable solids of the same size, shape, density as the MEM devices removed from the fluid flow stream.

The efficiency operations can also be executed for recognizing a threshold of expected efficiency for the solids control equipment. The computing device 114 can be communicatively coupled to an alarm system 514 via the bus 504. If the amount or types of MEM devices removed from the fluid flow stream by a component of solids control equipment or the efficiency of the solids control equipment is below a threshold, the processing device 502 can execute one or more operations for outputting an alarm, through the alarm system 514, in response to such conditions.

In some examples, the computing device 114 can also be communicatively coupled to a display device 510 via the bus 504. The display device can display data that may correspond to data received by the computing device 114 from a MEM reader. The display device may also display data that may correspond to data generated by executing an efficiency operation executed by the processing device 502.

The processing device 502 can also be communicatively coupled to the memory device 506 via the bus 504. The non-volatile memory device may include any type of memory that retains stored information when powered off. Non-limiting examples of the memory device 506 include EEPROM, flash memory, or any other type of non-volatile memory. In some examples, at least some of the memory device 506 can include a medium from which the processing device can read instructions 508. A computer-readable medium can include electronic, optical, magnetic, or other storage devices capable of providing the processing device 502 with computer-readable instructions or other program code. Non-limiting examples of a computer-readable medium include, but are not limited to, magnetic disks, memory chips, read-only memory ("ROM"), random-access memory ("RAM"), an ASIC, a configured processor, optical storage, or any other medium from which a computer processor can read instructions.

Figure 6:
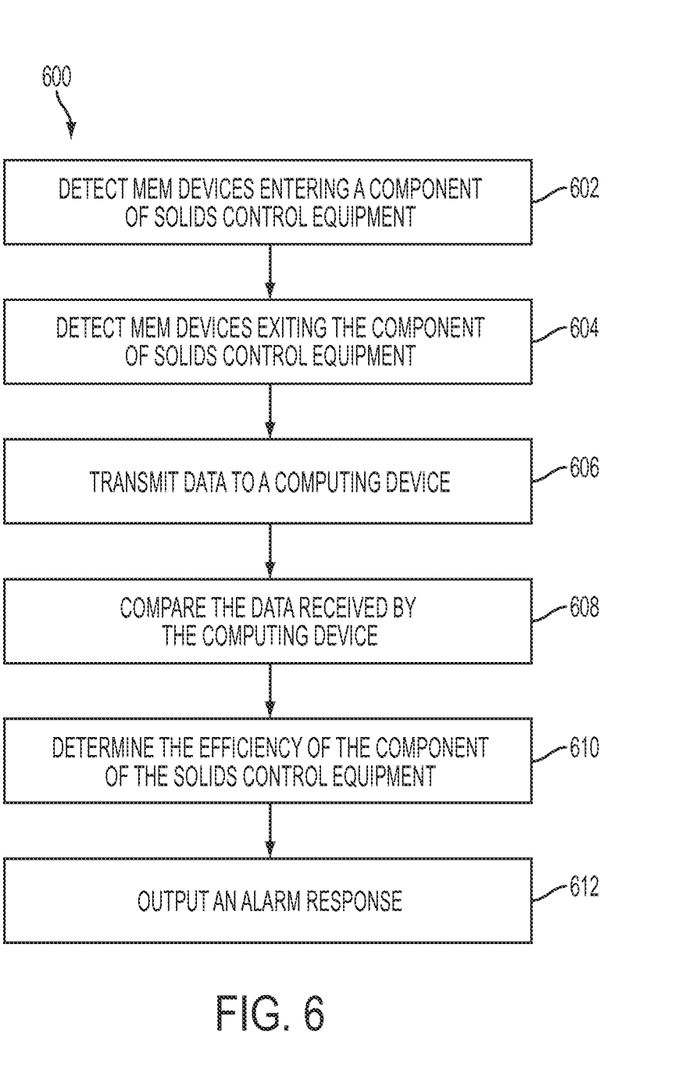
FIG. 6 is a flow chart showing an example of a process for monitoring removal of MEM devices from a fluid flow stream from a wellbore according to one example of the present disclosure.

FIG. 6 is a flow chart of an example of a process 600 for monitoring removal of MEM devices from a fluid flow stream from a wellbore.

In block 602, MEM devices entering a component of solids control equipment are detected. In some examples, a first MEM reader may detect MEM devices in a fluid flow stream from a wellbore prior to a fluid flow input of the component of solids control equipment.

The MEM devices may be of various sizes, shapes, and densities and may represent non-desirable solids in the fluid flow stream from the wellbore. The MEM devices may be disposable in the fluid flow stream from a wellbore. The MEM devices may be disposable in the fluid flow stream at any point in the fluid flow stream prior to the fluid flow stream entering a fluid flow input of a component of solids control equipment. The MEM devices may be disposable in the fluid flow stream in any manner, including without limitation, through manual disposal (e.g., manual labor) or through automated disposal (e.g., by an apparatus, device, machine, or the like).

The first MEM reader may detect an amount and types of MEM devices in the fluid flow stream prior to the fluid flow input of the component of solids control equipment through a communication link. In some examples, the communication link may be any link that facilitates communication between the individual MEM devices in the fluid flow stream prior to the fluid flow input and the first MEM reader. The communication link may be wireless and can include wireless interfaces.

In some examples, identification information for each MEM device may be stored on a microchip on the MEM device. The first MEM reader may detect the identification information for each MEM device in the fluid flow stream prior to the fluid flow input of the component of solids control equipment through the communication link.

In another example, the first MEM reader may detect an amount and types of MEM devices in the fluid flow stream prior to the fluid flow input through electromagnetic fields and energy. The MEM devices may be devices with RFID tags. The first MEM reader may be an RFID tag reader. Identification data may be stored within a microchip on the MEM devices. The MEM devices may transmit signals, through an electromagnetic field, to the first MEM reader. The first MEM reader may detect the MEM devices in the fluid flow stream prior to the fluid flow input by detecting the signals and interpreting the identification data stored on the MEM devices.

The first MEM reader may also detect individual MEM devices and store data that may be representative of a distribution of the amount and types of MEM devices of different sizes, shapes, and densities in the fluid flow stream prior to the fluid flow input.

In other examples, any reader for detecting or sensing MEM devices may detect the MEM devices entering the component of solids control equipment.

In block 604, MEM devices exiting a component of solids control equipment are detected. In some examples, a second MEM reader may detect MEM devices in the fluid flow stream from a wellbore subsequent to a fluid flow output of the component of solids control equipment.

The second MEM reader may detect an amount and types of MEM devices in the fluid flow stream subsequent to a fluid flow output of the component of solids control equipment. The second MEM reader may detect the identification information for each MEM device in the fluid flow stream subsequent to the fluid flow output through a communication link configured substantially the same as the communication link described above. The second MEM reader may also detect an amount and types of MEM devices in the fluid flow stream subsequent to the fluid flow output through electromagnetic fields and energy configured substantially the same as the electromagnetic fields and energy described above.

In some examples, the second MEM reader may detect individual MEM devices and store data that may be representative of a distribution of the amount and types of MEM devices of different sizes, shapes, and densities in the fluid flow stream subsequent to the fluid flow output.

In other examples, any reader for detecting or sensing MEM devices may detect the MEM devices exiting the component of solids control equipment.

In block 606, data is transmitted to a computing device. In some examples, a first MEM reader may transmit data to a computing device. The data may represent the amount and types of MEM devices in the fluid flow stream prior to the fluid flow input of the component of solids control equipment. The first MEM reader may transmit other data that represents a distribution of the amount and types of MEM devices of different sizes, shapes, and densities in the fluid flow stream prior to the fluid flow input.

A second MEM reader may also transmit data to the computing device. The data may represent the amount and types of MEM devices in the fluid flow stream subsequent to the fluid flow output of the component of solids control equipment. The second MEM reader may transmit other data that represents a distribution of the amount and types of MEM devices of different sizes, shapes, and densities in the fluid flow stream subsequent to the fluid flow output.

In block 608, the data transmitted to the computing device is compared. In some examples, the computing device may compare the data received from the first MEM reader and the second MEM reader. The computing device may compare the amount and types of MEM devices in the fluid flow stream prior to the fluid flow input and the amount and types of MEM devices in the fluid flow stream subsequent to the fluid flow output.

In block 610, the efficiency of the solids control equipment in removing MEM devices from a fluid flow stream is determined. In some examples, the computing device determines efficiency of the component of solids control equipment.

The computing device may determine the efficiency of the solids control equipment by determining an amount and types of MEM devices removed from the fluid flow stream by the component of solids control equipment. The computing device may also determine the efficiency of the solids control equipment by determining an amount and types of MEM devices of different sizes, shapes, and densities removed from the fluid flow stream by the component of solids control equipment.

The computing device may also determine the efficiency of the solids control equipment by determining an amount of MEM devices of a shape, size, or density, representative of non-desirable solids of the same size, shape, or density, removed from the fluid flow stream.

In some examples, the process 600 for monitoring removal of MEM devices from a fluid flow stream from a wellbore further includes, in block 612, the computing device outputting an alarm in response to determining that the amount of MEM devices removed from the fluid flow stream by the component of solids control equipment is below a threshold. The computing device may also output the alarm in response to determining that the efficiency of the solids control equipment is below a threshold.

Figure 7:
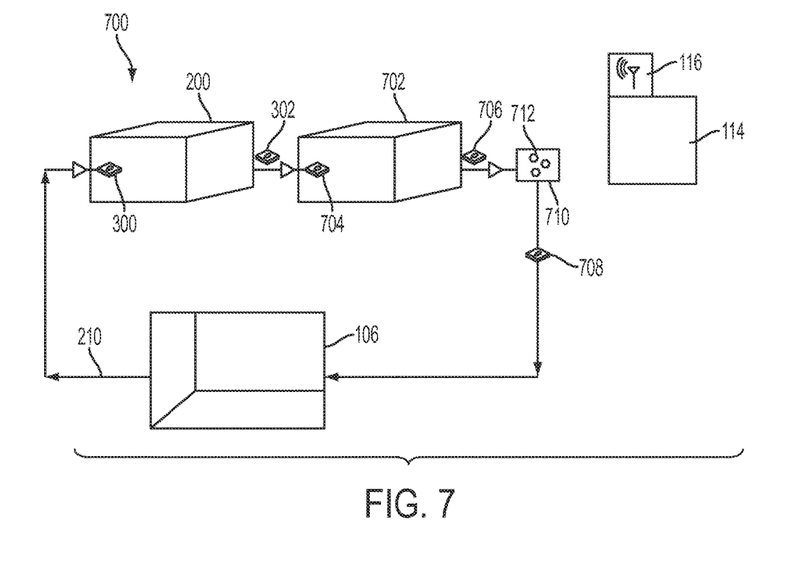
FIG. 7 is a schematic diagram showing a system for monitoring removal of MEM devices from a fluid flow stream from a wellbore according to one example of the present disclosure.

FIG. 7 is a schematic diagram of a system 700 for monitoring removal of MEM devices from a fluid flow stream from a wellbore, two components of solids control equipment 200, 702 and five MEM readers 300, 302, 704, 706, 708 along with a magnetic system 710 and a computing device 114 according to one example of the present disclosure.

In some examples, more than one component of solids control equipment may be used to separate and capture an amount and types of MEM devices from a fluid flow stream. Each component of solids control equipment may be independently associated with a first MEM reader and a second MEM reader for detecting MEM devices prior to the fluid flow input and subsequent to the fluid flow output.

A MEM reader 300 may detect an amount and types of MEM devices in a fluid flow stream 210 from a wellbore 106 prior to a fluid flow input of a component of solids control equipment 200. The MEM reader 300 may transmit data to a computing device 114 via a communication device 116.

A MEM reader 302 may detect an amount and types of MEM devices in the fluid flow stream 210 subsequent to a fluid flow output of the component of solids control equipment 200. The MEM reader 302 may transmit data to the computing device 114 via the communication device 116.

A MEM reader 704 may detect an amount and types of MEM devices in the fluid flow stream 210 prior to a fluid flow input of another component of solids control equipment

702. The MEM reader 704 may transmit data to the computing device 114 via the communication device 116.

A MEM reader 706 may detect an amount and types of MEM devices in the fluid flow stream 210 prior to a fluid flow output of the component of solids control equipment 702. The MEM reader 706 may transmit data to the computing device 114 via the communication device 116

A magnetic system 710 may be a magnetic system including at least one magnet. The magnetic system may be positionable subsequent to the MEM reader 706. The magnetic system 710 may retrieve any MEM devices 712 remaining in the fluid flow stream 210 subsequent to the fluid flow output of the component of solids control equipment 702.

A MEM reader 708 may be positioned near the fluid flow stream 210 and subsequent to the fluid flow output of the component of solids control equipment 702 and the MEM reader 706. The MEM reader 708 may detect at least a subset of the amount and types of MEM devices in the fluid flow stream 210 returning to the wellbore 106 after exiting the fluid flow output of the component of solids control equipment 702.

Various types of systems can be used for monitoring removal of MEM devices from a fluid flow stream from a wellbore to assess efficiency of solids control equipment. The following are examples.

EXAMPLE #1

A system can use a component of solids control equipment that is operable in a drill rig system for a wellbore. The component of solids control equipment can have a fluid flow input and a fluid flow output. The system can also use MEM devices and a MEM reader. The MEM devices can be of different sizes, shapes, and densities and can be disposable in a fluid flow stream from the wellbore. The MEM reader can be positioned near the fluid flow stream and the fluid flow output for detecting the MEM devices in the fluid flow stream. The MEM reader can also be positioned near the fluid flow stream and between the fluid flow output and the wellbore for detecting the MEM devices in the fluid flow stream. The system can further include a processing module comprising a non-transitory computer-readable medium with machine-readable code for determining an amount and types of the MEM devices removed from the fluid flow stream by the component of solids control equipment.

EXAMPLE #2

The system of Example #1 may feature the MEM reader being a first MEM reader and a second MEM reader. The first MEM reader being positioned near the fluid flow stream and between the fluid flow input and the wellbore for detecting the MEM devices in the fluid flow stream. The second MEM reader being positioned near the fluid flow stream and the fluid flow output for detecting at least a subset of the MEM devices in the fluid flow stream. The second MEM reader may also be positioned near the fluid flow stream and between the fluid flow output and the wellbore for detecting at least a subset of the MEM devices in the fluid flow stream.

EXAMPLE #3

The system of any of Examples #1-2 may feature the component of solids control equipment including at least one of a shale shaker, a desander, a desilter, a centrifuge, or a mud cleaner.

EXAMPLE #4

The system of any of Examples #1-3 may feature the sizes, shapes, and densities of the MEM devices being representative of at least some non-desirable solids in the fluid flow stream from the wellbore.

EXAMPLE #5

The system of any of Examples #1-4 may feature the processing module being communicatively coupled to (i) the first MEM reader for receiving data corresponding to the amount and types of MEM devices in the fluid flow stream prior to the fluid flow input and (ii) the second MEM reader for receiving data corresponding to the amount and types of MEM devices in the fluid flow stream subsequent to the fluid flow output.

EXAMPLE #6

The system of any of Examples #1-5 may feature the processing module including machine-readable code for comparing the amount and types of MEM devices in the fluid flow stream prior to the fluid flow input and the amount and types of MEM devices in the fluid flow stream subsequent to the fluid flow output to determine the amount and types of the MEM devices removed from the fluid flow stream by the component of solids control equipment.

EXAMPLE #7

The system of any of Examples #1-6 may feature the processing module including machine-readable code for outputting an alarm in response to determining that the amount or types of MEM devices removed from the fluid flow stream by the component of solids control equipment is below a threshold.

EXAMPLE #8

The system of any of Examples #1-7 may feature the first MEM reader being positioned near the fluid flow stream and between the fluid flow input and the wellbore for detecting an amount and types of MEM devices of different sizes, shapes, and densities in the fluid flow stream prior to the fluid flow input. The system may also feature the second MEM reader being positioned near the fluid flow stream and between the fluid flow output and the wellbore for detecting at least a subset of the amount and types of MEM devices of different sizes, shapes, and densities in the fluid flow stream subsequent to the fluid flow output.

EXAMPLE #9

The system of any of Examples #1-8 may feature the processing module being communicatively coupled to (i) the first MEM reader for receiving data corresponding to a distribution of the amount and types of MEM devices of different sizes, shapes, and densities in the fluid flow stream prior to the fluid flow input and (ii) the second MEM reader for receiving data corresponding to a distribution of the amount and types of MEM devices of different sizes, shapes, and densities in the fluid flow stream subsequent to the fluid flow output.

EXAMPLE #10

The system of any of Examples #1-9 may feature the processing module including machine-readable code for comparing the distribution of the amount and types of MEM devices of different sizes, shapes, and densities in the fluid flow stream prior to the fluid flow input and subsequent to the fluid flow output. The system may also feature using the comparison to determine the amount and types of MEM devices of different sizes, shapes, and densities removed from the fluid flow stream by the component of solids control equipment.

EXAMPLE #11

The system of any of Examples #1-10 may feature the second MEM reader being positioned near the fluid flow stream and between the fluid flow output and the wellbore and the system further using a third MEM reader. The third MEM reader can be positioned near the fluid flow stream and subsequent to the fluid flow output and the second MEM reader for detecting at least a subset of the MEM devices in the fluid flow stream returning to the wellbore after exiting the fluid flow output.

EXAMPLE #12

The system of any of Examples #1-11 may feature a magnetic system positioned subsequent to the second MEM reader. The magnetic system can include at least one magnet for retrieving any MEM devices remaining in the fluid flow stream subsequent to the fluid flow output.

EXAMPLE #13

A method can include detecting, by a first MEM reader, MEM devices of different sizes, shapes, and densities in a fluid flow stream from a wellbore prior to a fluid flow input of a component of solids control equipment. The method can also include detecting, by a second MEM reader, at least a subset of the MEM devices in the fluid flow stream subsequent to a fluid flow output of the component of solids control equipment. The method can further include determining, by a processing module comprising a non-transitory computer-readable medium embodying machine-readable code, an amount and types of the MEM devices removed from the fluid flow stream by the component of solids control equipment.

EXAMPLE #14

The method of Example #13 may feature transmitting first data from the first MEM reader to the processing module. The first data can represent an amount and types of MEM devices in the fluid flow stream prior to the fluid flow input. The method may also feature transmitting second data from the second MEM reader to the processing module. The second data can represent an amount and types of MEM devices in the fluid flow stream subsequent to the fluid flow output.

EXAMPLE #15

The method of any of Examples #13-14 may feature comparing, by the processing module, the amount and types of MEM devices in the fluid flow stream prior to the fluid flow input and the amount and types of MEM devices in the fluid flow stream subsequent to the fluid flow output. The method may also feature using the comparison to determine an amount and types of the MEM devices removed from the fluid flow stream by the component of solids control equipment.

EXAMPLE #16

The method of any of Examples #13-15 may feature transmitting first data from the first MEM reader to the processing module. The first data can represent a distribution of the amount and types of MEM devices of different sizes, shapes, and densities in the fluid flow stream prior to the fluid flow input. The method may also feature transmitting second data from the second MEM reader to the processing module. The second data can represent a distribution of the amount and types of MEM devices of different sizes, shapes, and densities in the fluid flow stream subsequent to the fluid flow output.

EXAMPLE #17

The method of any of Examples #13-16 may feature comparing, by the processing module, the distribution of the amount and types of MEM devices of different sizes, shapes, and densities in the fluid flow stream prior to the fluid flow input and subsequent to the fluid flow output. The method may also feature using the comparison to determine an amount and types of MEM devices of different sizes, shapes, and densities removed from the fluid flow stream by the component of solids control equipment.

EXAMPLE #18

The method of any of Examples #13-17 may feature outputting an alarm in response to determining that the amount or types of MEM devices removed from the fluid flow stream by the component of solids control equipment is below a threshold.

EXAMPLE #19

The method of any of Examples #13-18 may feature retrieving, by a magnetic system having at least one magnet, any MEM devices remaining in the fluid flow stream subsequent to the fluid flow output.

EXAMPLE #20

A system can use a first MEM reader and a second MEM reader. The first MEM reader can be positioned near a fluid flow stream from a wellbore for detecting an amount of MEM devices in the fluid flow stream prior to a fluid flow input of a component of solids control equipment. The component of solids control equipment can be operable with a drill rig system for the wellbore. The second MEM reader can be positioned near the fluid flow stream for detecting an amount of MEM devices in the fluid flow stream subsequent to a fluid flow output of the component of solids control equipment. The first MEM reader and the second MEM reader can be communicatively coupled with a processing module to determine an amount of MEM devices removed from the fluid flow stream by the component of solids control equipment.

EXAMPLE #21

The system of Example #20 may further include MEM devices of different sizes, shapes, and densities disposable in the fluid flow stream.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A system comprising:
    a component of solids control equipment operable in a drill rig system for a wellbore, the component of solids control equipment having a fluid flow input and a fluid flow output;
    micro-electro-mechanical ("MEM") devices disposable in a fluid flow stream from the wellbore, the MEM devices being of various types differing in at least one of sizes, shapes, or densities so as to be representative of a plurality of non-desirable solids in the wellbore;
    a first MEM reader positionable proximate to the fluid flow stream and between the fluid flow input and the wellbore for detecting an amount and types of the MEM devices in the fluid flow stream prior to the fluid flow input;
    a second MEM reader positionable proximate to the fluid flow stream and the fluid flow output for detecting at least an amount and types of a subset of the MEM devices in the fluid flow stream subsequent to the fluid flow output; and
    a processing module comprising a non-transitory computer-readable medium with machine-readable code for comparing the amount and types of the MEM devices in the fluid flow stream prior to the fluid flow input and the amount and types of MEM devices in the fluid flow stream subsequent to the fluid flow output to determine the amount and types of the MEM devices removed from the fluid flow stream by the component of solids control equipment and for outputting, in response to the comparing, an indication of an efficiency of the component of solids control equipment in removing the plurality of non-desirable solids.

2. The system of claim 1, wherein the component of solids control equipment includes at least one of a shale shaker, a desander, a desilter, a centrifuge, or a mud cleaner.

3. The system of claim 1, wherein the processing module is communicatively coupled to the first MEM reader for receiving data corresponding to the amount and types of MEM devices in the fluid flow stream prior to the fluid flow input and the processing module is communicatively coupled to the second MEM reader for receiving data corresponding to the amount and types of MEM devices in the fluid flow stream subsequent to the fluid flow output.

4. The system of claim 1, wherein the outputting comprises producing an alarm.

5. The system of claim 1, wherein the processing module is communicatively coupled to the first MEM reader for receiving data corresponding to a distribution of the various types of MEM devices, and densities in the fluid flow stream prior to the fluid flow input and the processing module is communicatively coupled to the second MEM reader for receiving data corresponding to a distribution of the types of MEM devices in the fluid flow stream subsequent to the fluid flow output.

6. The system of claim 5, wherein the processing module comprises machine-readable code for comparing the distribution of the amount and types of MEM devices in the fluid flow stream prior to the fluid flow input and the distribution of the amount and types of MEM devices in the fluid flow stream subsequent to the fluid flow output to determine a distribution of the efficiency of the plurality of non-desirable solids removed from the fluid flow stream by the component of solids control equipment.

7. The system of claim 1, wherein the second MEM reader is positionable proximate to the fluid flow stream and between the fluid flow output and the wellbore and further comprising:
    a third MEM reader positionable proximate to the fluid flow stream and subsequent to the fluid flow output and subsequent to the second MEM reader for detecting at least a subset of the MEM devices in the fluid flow stream returning to the wellbore after exiting the fluid flow output.

8. The system of claim 1, further comprising:
    a magnetic system, positionable subsequent to the second MEM reader, the magnetic system having at least one magnet for retrieving any MEM devices remaining in the fluid flow stream subsequent to the fluid flow output.

9. A method comprising:
    detecting, by a first micro-electro-mechanical ("MEM") reader, an amount and types of MEM devices in a fluid flow stream from a wellbore prior to a fluid flow input of a component of solids control equipment, the MEM devices being of various types differing in at least one of sizes, shapes, or densities so as to be representative of a plurality of non-desirable solids in the wellbore;
    detecting, by a second MEM reader, at least an amount and types of a subset of the MEM devices in the fluid flow stream subsequent to a fluid flow output of the component of solids control equipment; and
    determining, by a processing module comprising a non-transitory computer-readable medium embodying machine-readable code, an efficiency of the component of solids control equipment in removing the plurality of non-desirable solids by comparing the amount and types of MEM devices in the fluid flow stream prior to the fluid flow input and the amount and types of MEM devices in the fluid flow stream subsequent to the fluid flow output.

10. The method of claim 9, further comprising:
    transmitting first data from the first MEM reader to the processing module, the first data corresponding to a distribution of the various types of MEM devices and densities in the fluid flow stream prior to the fluid flow input; and
    transmitting second data from the second MEM reader to the processing module, the second data corresponding to a distribution of the types of MEM devices in the fluid flow stream subsequent to the fluid flow output.

11. The method of claim 10, further comprising:
    comparing, by the processing module, the distribution of the amount and types of MEM devices in the fluid flow stream prior to the fluid flow input and the distribution of the amount and types of MEM devices in the fluid flow stream subsequent to the fluid flow output to determine a distribution of the efficiency of the component of solids control equipment in removing the plurality of non-desirable solids from the fluid flow stream.

12. The method of claim 9, further comprising:
    outputting, by the processing module, an alarm in response to the efficiency of the component of solids control equipment in removing the plurality of non-desirable solids being below a threshold.

13. The method of claim 9, further comprising retrieving, by a magnetic system having at least one magnet, any MEM devices remaining in the fluid flow stream subsequent to the fluid flow output.

14. A system comprising:
   a first micro-electro-mechanical ("MEM") reader positionable proximate to a fluid flow stream from a wellbore for detecting an amount and types of MEM devices in the fluid flow stream prior to a fluid flow input of a component of solids control equipment operable with a drill rig system for the wellbore, the MEM devices being of various types representative of a plurality of non-desirable solids in the wellbore; and
   a second MEM reader positionable proximate to the fluid flow stream for detecting an amount and types of MEM devices in the fluid flow stream subsequent to a fluid flow output of the component of solids control equipment, the first MEM reader and the second MEM reader being communicatively coupled with a processing module to determine an efficiency of the component of solids control equipment in removing the plurality of non-desirable solids by comparing the amount and types of MEM devices in the fluid flow stream prior to the fluid flow input and the amount and types of MEM devices in the fluid flow stream subsequent to the fluid flow output.

15. The system of claim 14, further comprising the MEM devices disposable in the fluid flow stream, the various types of MEM devices differing in at least one of sizes, shapes or densities.

* * * * *